(12) United States Patent
Tanaka

(10) Patent No.: US 10,150,785 B2
(45) Date of Patent: Dec. 11, 2018

(54) METHOD FOR PRODUCING DIALKYLAMINOSILANE

(71) Applicant: JNC CORPORATION, Tokyo (JP)

(72) Inventor: Toru Tanaka, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 15/552,804

(22) PCT Filed: Jan. 22, 2016

(86) PCT No.: PCT/JP2016/051787
§ 371 (c)(1),
(2) Date: Aug. 23, 2017

(87) PCT Pub. No.: WO2016/152226
PCT Pub. Date: Sep. 29, 2016

(65) Prior Publication Data
US 2018/0044358 A1 Feb. 15, 2018

(30) Foreign Application Priority Data
Mar. 24, 2015 (JP) .................. 2015-061523

(51) Int. Cl.
*C07F 7/10* (2006.01)
*C07F 7/02* (2006.01)
(52) U.S. Cl.
CPC ............... *C07F 7/10* (2013.01); *C07F 7/025* (2013.01)
(58) Field of Classification Search
None
See application file for complete search history.

(56) References Cited

U.S. PATENT DOCUMENTS

| | | | |
|---|---|---|---|
| 3,467,686 A | 9/1969 | Creamer | |
| 3,927,057 A | 12/1975 | Takamizawa et al. | |
| 4,255,348 A | 3/1981 | Herdle et al. | |
| 4,598,161 A | 7/1986 | Farnham et al. | |
| 2004/0210071 A1 | 10/2004 | Itsuki | |
| 2012/0021127 A1 | 1/2012 | Sato et al. | |
| 2012/0128897 A1 | 5/2012 | Xiao et al. | |
| 2012/0165564 A1* | 6/2012 | Hamada .................. | C07F 7/10 556/410 |

FOREIGN PATENT DOCUMENTS

| | | |
|---|---|---|
| JP | S505332 | 1/1975 |
| JP | S5668686 | 6/1981 |
| JP | S59184157 | 10/1984 |
| JP | 2001002682 | 1/2001 |
| JP | 2004250431 | 9/2004 |
| JP | 2010225663 | 10/2010 |
| JP | 2012025733 | 2/2012 |
| JP | 2012136472 | 7/2012 |
| JP | 2015208718 | 11/2015 |
| WO | 2015146103 | 10/2015 |

OTHER PUBLICATIONS

B. J. Aylett et al.,"Dimethylamino-derivatives of monosilane. Preparation, some physical and chemical properties, and pyrolysis",Journal of the Chemical Society,1964,pp. 3429-3436.
"International Search Report (Form PCT/ISA/210) of PCT/JP2016/051787", dated Apr. 12, 2016, with English translation thereof, pp. 1-4.
J. Pikies et al., "Elektronische and sterische Effekte in 29Si-NMR-Spektren von Amino-substituierten Silanen", Z. Anorg. Allg. Chem., Jan. 1985, pp. 173-182.
K. Trommer et al., "Generation and Investigation of Various (Alkylamino)phenylsilyllithium Species—Behaviour in Coupling Reactions with Chlorosilanes", J. prakt. Chem, May 1998, pp. 557-561.
K. Issleib et al., "5-Organo-1,5-Phospha-Silabicyclo[3. 3.0]Octane-Synthese und Reaktionsverhalten", Phosphorus and Sulfur, Jun. 1984, pp. 367-373.
"Search Report of Europe Counterpart Application", dated Jul. 2, 2018, p. 1-p. 4.
"Office Action of Europe Counterpart Application", dated Jul. 23, 2018, p. 1-p. 6.

* cited by examiner

*Primary Examiner* — Clinton A Brooks
*Assistant Examiner* — Kofi Adzamli
(74) *Attorney, Agent, or Firm* — JCIPRNET

(57) ABSTRACT

In a method for synthesizing dialkylaminosilane from a reaction of dialkylamine with chlorosilane as the method for producing dialkylaminosilane, a large amount of dialkylamine hydrochloride is produced as a by-product, in addition to objective dialkylaminosilane. Therefore, upon obtaining objective dialkylaminosilane, reduction of volumetric efficiency caused by a large amount of a solvent is prevented, and dialkylaminosilane is produced at a low cost and in a large amount. Dialkylaminosilane having a small halogen content is produced with high volumetric efficiency by using, as a solvent upon allowing dialkylamine to react with chlorosilane, an aprotic polar solvent having high solubility in dialkylamine hydrochloride and metal chloride each produced as a by-product by the reaction, and straight-chain or branched hydrocarbon having high solubility in dialkylaminosilane and hard to dissolve a halogen compound therein.

9 Claims, 1 Drawing Sheet

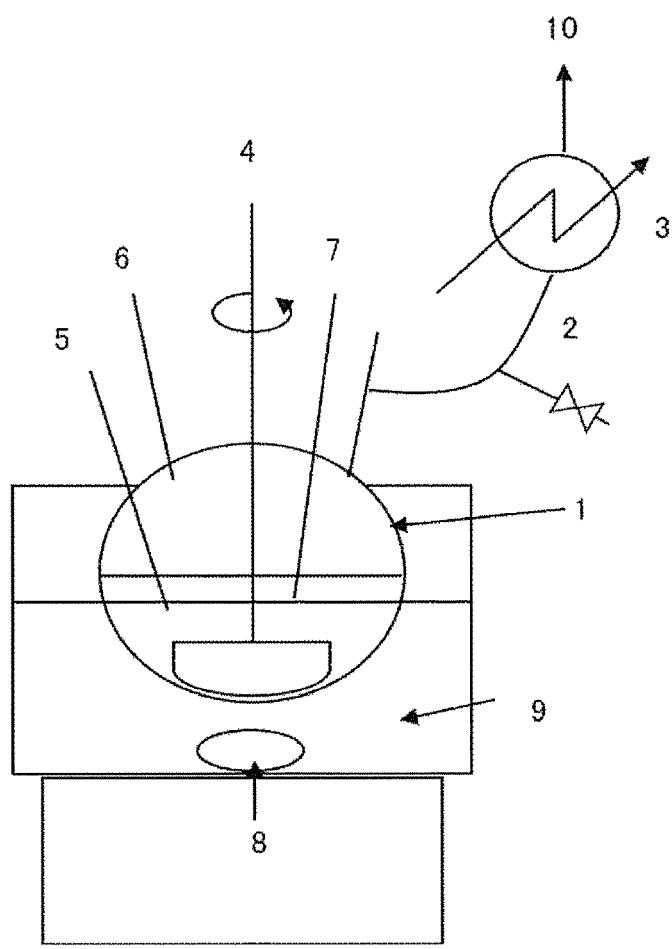

METHOD FOR PRODUCING DIALKYLAMINOSILANE

CROSS-REFERENCE TO RELATED APPLICATION

This application is a 371 application of the international PCT application serial no. PCT/JP2016/051787, filed on Jan. 22, 2016, which claims the priority benefit of Japan application no. 2015-061523, filed on Mar. 24, 2015. The entirety of each of the above-mentioned patent applications is hereby incorporated by reference herein and made a part of this specification.

TECHNICAL FIELD

The invention relates to a method for producing high-purity dialkylaminosilane. More specifically, the invention relates to a method for efficiently producing dialkylaminosilane from dialkylamine and chlorosilane by using, as a solvent, a mixed solvent of straight-chain hydrocarbon or branched hydrocarbon and an aprotic polar solvent.

BACKGROUND ART

Dialkylaminosilane is a compound having a silicon atom and a nitrogen atom in a molecule. Particularly, a high-purity product having a low content of highly corrosive halogen including chlorine has been recently desired in an electronics & IT materials area, such as a semiconductor insulating film material and a super-water repellent agent on a silicon wafer surface, and a method for efficiently producing the product at a low cost has been required.

As a method for producing dialkylaminosilane, a method for synthesizing dialkylaminosilane from a reaction of dialkylamine with chlorosilane is known (Non-patent literature No. 1). However, a large amount of dialkylamine hydrochloride is produced as a by-product, in addition to objective dialkylaminosilane, and therefore in order to obtain dialkylaminosilane, reduction of volumetric efficiency caused by a large amount of a solvent has been required to be prevented, or solid-liquid separation operation such as filtration or decantation has been required.

Patent literature No. 1 discloses a method for separating dialkylamine hydrochloride produced in a large amount as a by-product, without performing solid-liquid separation such as filtration, by adding an alkaline aqueous solution thereto to dissolve dialkylamine hydrochloride in the alkaline aqueous solution, and extracting the resultant hydrochloride into an aqueous layer.

Patent literature No. 2 discloses a method for allowing dialkylamine hydrochloride produced in a large amount as a by-product to react with metal (such as magnesium), while temperature is controlled, into dialkylamine, metal chloride (such as magnesium chloride) and hydrogen to regenerate dialkylamine and to reduce an amount of salt.

Patent literature Nos. 3 and 4 disclose a method for directly producing dialkylaminosilane from metallic silicon and dialkylamine in the presence of a copper catalyst, in which no chlorosilane is used, and therefore no dialkylamine hydrochloride is formed and a halogen content is small.

CITATION LIST

Patent Literature

Patent literature No. 1: JP S50-5332 A
Patent literature No. 2: US 3467686 B
Patent literature No. 3: JP S56-68686 A
Patent literature No. 4: JP 2001-2682 A Non-Patent Literature Non-patent literature No. 1: J. Chem. Soc., 1964, 3429-3436

SUMMARY OF INVENTION

Technical Problem

In the production method in Patent literature No. 1, dialkylaminosilane is liable to be hydrolyzed, resulting in significant reduction of a yield by bringing dialkylaminosilane that easily reacts with water into contact with an alkaline aqueous solution.

In Patent literature Nos. 3 and 4, structure of dialkylaminosilane is limited into a compound only having a hydrogen group and a dimethylamino group as a substituent, resulting in a lack of general versatility.

Moreover, Patent literature No. 2 has a convenience in which dialkylamine hydrochloride produced by a reaction can be allowed to react with metal, while temperature is controlled, to reduce an amount in the form of metal chloride, and also dialkylaminosilane can be produced in a substantially stoichiometrically equivalent amount from dialkylamine. However, if a compound having a large number of substitution of chlorine in chlorosilane is applied, a large load is liable to be applied on solid-liquid separation also in metal chloride. Therefore, a desire has been expressed for a method for efficiently producing dialkylaminosilane, in which the method corresponds to various dialkylaminosilane, an amount of precipitation of salt is suppressed, and also a halogen content is suppressed.

Solution to Problem

The present inventors have found that, in a process of producing dialkylaminosilane from dialkylamine and chlorosilane, an amount of precipitation of salt and a halogen content are significantly different depending on a kind of a solvent and a combination thereof.

The present inventors have found that dialkylaminosilane having a small halogen content can be obtained with high volumetric efficiency by using, as a solvent upon allowing dialkylamine to react with chlorosilane, an aprotic polar solvent having high solubility in dialkylamine hydrochloride and metal chloride each produced as a by-product by a reaction, and straight-chain or branched hydrocarbon that has high solubility in dialkylaminosilane and is hard to dissolve a halogen compound therein.

The invention is constituted of items 1 to 10 described below.

Item 1. A method for producing dialkylaminosilane, by allowing dialkylamine to react with chlorosilane in a mixed solvent of an aprotic polar solvent and a solvent of straight-chain or branched hydrocarbon.

Item 2. The method for producing dialkylaminosilane according to item 1, wherein metal is added thereto in a reaction of dialkylamine with chlorosilane.

Item 3. The method for producing dialkylaminosilane according to item 1 or 2, wherein the solvent of straight-chain or branched hydrocarbon is used in an amount of 0.2 to 10 times in weight based on chlorosilane.

Item 4. The method for producing dialkylaminosilane according to any one of items 1 to 3, wherein the aprotic polar solvent is used in an amount of 0.2 to 10 times in weight based on chlorosilane.

Item 5. The method for producing dialkylaminosilane according to any one of items 1 to 4, wherein dialkylamine is represented by a chemical formula:

wherein, R1 and R2 are independently a straight-chain alkyl group having 1 to 6 carbons, a branched alkyl group having 3 to 6 carbons or a phenyl group.

Item 6. The method for producing dialkylaminosilane according to any one of items 1 to 5, wherein chlorosilane is represented by a chemical formula:

$R3_n—Si—Cl_{(4-n)}$ wherein, R3 is hydrogen, a straight-chain alkyl group having 1 to 6 carbons, a branched alkyl group having 3 to 6 carbons or a phenyl group, and n is an integer from 0 to 3.

Item 7. The method for producing dialkylaminosilane according to any one of items 1 to 6, wherein the aprotic polar solvent is at least one selected from acetonitrile, tetrahydrofuran (THF), dimethylformamide (DMF), acetone, dichloromethane, dimethyl sulfoxide (DMSO), dioxane, dimethylacetamide and hexamethylphosphoramide (HMPA).

Item 8. The method for producing dialkylaminosilane according to any one of items 1 to 7, wherein the aprotic polar solvent is acetonitrile.

Item 9. The method for producing dialkylaminosilane according to any one of items 1 to 8, wherein the solvent of straight-chain or branched hydrocarbon is straight-chain hydrocarbon having 5 to 40 carbons or branched hydrocarbon having 5 to 40 carbons.

Item 10. The method for producing dialkylaminosilane according to any one of items 2 to 9, wherein the metal to be added is at least one selected from magnesium, calcium and zinc.

Advantageous Effects of Invention

According to the invention, volumetric efficiency can be improved and a load of solid-liquid separation can be reduced by dissolving dialkylamine hydrochloride or metal chloride into a solvent, and also high-quality dialkylaminosilane having a relatively small halogen content can be produced stably, efficiently and at a low cost, irrespective of a kind of chlorosilane. Moreover, if dialkylaminosilane according to the invention is applied, a halogen content in a reaction mixture is small, and therefore a yield in distillation is satisfactory, and high-quality dialkylaminosilane can be efficiently obtained.

DESCRIPTION OF EMBODIMENTS

In a process of producing dialkylaminosilane, existence of a solvent system has been revealed, in which dialkylamine hydrochloride or metal chloride can be dissolved in a solvent by selecting the solvent and a halogen content contained in dialkylaminosilane can be reduced.

Specific examples of the solvent in which dialkylamine hydrochloride and metal chloride are dissolved include, as an aprotic and high-polar solvent, acetonitrile, tetrahydrofuran (THF), dimethylformamide (DMF), acetone, dichloromethane, dimethyl sulfoxide (DMSO), dioxane, dimethylacetamide and hexamethylphosphoramide (HMPA), and in addition thereto, ethers such as diethyl ether and ethylene glycol dimethyl ether, halogen type hydrocarbon such as chloroform, ethers such as ethyl acetate and methyl formate, and tertiary amine such as triethylamine and tetramethylethylenediamine can be used.

Moreover, specific examples of the solvent for reducing the halogen content in dialkylaminosilane include straight-chain or branched hydrocarbon such as n-hexane, n-heptane and n-octane.

The aprotic polar solvent and the solvent of straight-chain or branched hydrocarbon include a case where a single solvent being the straight-chain or branched hydrocarbon may be used, or dialkylamine and chlorosilane are allowed to react in a mixed solvent of the straight-chain or branched hydrocarbon and the aprotic polar solvent.

When the single solvent of the straight-chain or branched hydrocarbon is used, dialkylamine hydrochloride is completely dissolved in the solvent, depending on temperature and an amount of addition of the aprotic polar solvent, by adding the aprotic polar solvent thereto after a reaction, and a straight-chain or branched hydrocarbon layer including dialkylaminosilane and an aprotic polar solvent layer including dialkylamine hydrochloride can be obtained by liquid-liquid separation.

Metal such as magnesium is added thereto before the reaction to allow the metal to react therewith at 50° C. or higher, preferably 80° C. or higher. Thus, dialkylamine hydrochloride produced as a by-product on the way of the reaction is allowed to react with the metal such as magnesium, and can be converted into metal chloride such as magnesium chloride. An amount of salt in the form of dialkylamine hydrochloride is reduced by half by conversion into metal chloride, the solvent is further reduced, and an amount of use of dialkylamine can be reduced. Moreover, metal chloride such as magnesium chloride has high solubility in the aprotic polar solvent, and can be completely dissolved in the solvent depending on temperature and an amount of the solvent, in a manner similar to dialkylamine hydrochloride.

FIG. 1 is a configuration diagram showing an ordinary experimental apparatus suitable for executing a method for producing dialkylaminosilane according to the invention.

A reaction vessel is assembled by arranging, for a glass flask equipped with 5 necks, a Dimroth condenser tube, a reflux head, a two-way cock for removing a reflux liquid, a content sampling tube, a stirrer, a thermometer and a dialkylamine feed port.

Dialkylaminosilane is decomposed by moisture, and therefore the moisture in the solvent and the apparatus significantly affects a yield. The moisture can be reduced by, as a dewatering method, adsorption by a molecular sieve or the like in the solvent, or in the apparatus, the moisture can be eliminated by azeotropic dewatering by using a solvent forming an azeotrope with water, such as acetonitrile and octane, and refluxing the solvent, and also the moisture can be reduced by allowing the metal such as magnesium to react with water.

Several combinations of the straight-chain or branched hydrocarbon and the aprotic polar solvent, being the solvent, and the metal such as magnesium are considered, but four methods described below are preferred. A first method is a case where three of the straight-chain or branched hydrocarbon, the aprotic polar solvent and the metal such as magnesium are added thereto during start of the reaction, a second method is a case where the straight-chain or branched hydrocarbon and the metal such as magnesium are charged thereinto during start of the reaction, and the aprotic polar solvent is added thereto after completion of feeding dialkylamine, a third method is a case where the straight-chain or branched hydrocarbon and the aprotic polar solvent are charged thereinto during start of the reaction without adding the metal such as magnesium, and a fourth method is a case where only the straight-chain or branched hydrocarbon is charged thereinto before the reaction without charging the metal such as magnesium thereinto, and the aprotic polar solvent is added thereto after completion of feeding dialkylamine. The above methods can be appropriately selected depending on a kind of chlorosilane and dialkylamine.

The case where the straight-chain or branched hydrocarbon, the aprotic polar solvent, and the metal such as magnesium are charged thereinto before the reaction, being one embodiment of the invention, will be described below. Dewatering in the apparatus is performed by charging the straight-chain or branched hydrocarbon, the aprotic polar solvent and the metal such as magnesium into the 5-neck flask, and then preferably heating the resulting mixture to cause azeotropic dewatering, or allowing magnesium to react with water, or performing both actions thereof. As the amount of the solvent, the straight-chain hydrocarbon is preferably 0.2 to 10 times (in weight), and the aprotic polar solvent is preferably 0.2 to 10 times based on chlorosilane. Moreover, the metal such as magnesium is preferably equivalent to 0.5 times based on chlorine in chlorosilane. After dewatering, an internal temperature is decreased to room temperature, and chlorosilane is charged into the 5-neck flask. An initial temperature for the reaction is set according to a boiling point of chlorosilane. A state in which chlorosilane is not refluxed is preferred. When a predetermined temperature is kept, dialkylamine is fed thereinto. In particular, dialkylamine is allowed into either a gas phase portion or a liquid phase portion. When the apparatus is small and stirring is strong, the reaction is sufficiently caused in feed into the gas phase, but when the apparatus is large and stirring is weak, dialkylamine is preferably fed into the liquid phase portion. When dialkylamine is fed thereinto by one-third to one half of a predetermined amount, the temperature is adjusted to 50° C., and if possible, to 80° C. or higher to allow dialkylamine hydrochloride to react with the metal such as magnesium. The above reaction is an exothermic reaction, and hydrogen and dialkylamine are produced. While chlorosilane remains, dialkylamine produced reacts with chlorosilane to have no problem. However, in a state in which the reaction of all of chlorosilane is completed, and also when dialkylamine having a low boiling point, or the like is used as dialkylamine, gas passage of the Dimroth condenser tube is liable to be sealed with a liquid of dialkylamine to cause an increase in internal pressure, and therefore enough attention is required to be paid. An end point of the reaction can be confirmed by settlement of heat generation when dialkylamine is entered therein in an amount equivalent or more based on chlorosilane.

Dialkylamine hydrochloride or metal chloride such as magnesium chloride is completely dissolved therein depending on the amount of the solvent and the temperature into two layers of a solvent layer of the straight-chain or branched hydrocarbon containing dialkylaminosilane, and the aprotic polar solvent layer containing dialkylamine hydrochloride or metal chloride such as magnesium chloride in a large amount, and the liquids in the above layers can be separated. Moreover, when the amount of the solvent is small or the temperature is low, dialkylamine hydrochloride or metal chloride such as magnesium chloride precipitates as a solid component, but the aprotic polar solvent having the high solubility is added thereto, and therefore salt having good solid-liquid separability is produced. Dialkylaminosilane containing the straight-chain or branched hydrocarbon can be obtained by performing the solid-liquid separation and then separating the liquids.

In dialkylaminosilane containing the straight-chain or branched hydrocarbon obtained by separating the liquids, the halogen content can be suppressed at a low level by a nonpolar effect of the straight-chain or branched hydrocarbon. Although a level depends on an amount of the straight-chain or branched hydrocarbon or a kind of dialkylaminosilane, a reaction raw liquid having a halogen content (chlorine component) of several ppm to several tens of ppm is obtained. High-quality dialkylaminosilane having a low halogen content (chlorine component) can be obtained by adding, as a dehalogenation (chlorination) agent, a methanol solvent of sodium methoxide, metal alkoxide such as potassium tert-butoxide, and an organometallic compound such as butyllithium and methyl Grignard to the reaction raw liquid, and rectifying the resulting mixture.

BRIEF DESCRIPTION OF DRAWINGS

FIG. 1 shows an apparatus diagram suitable for executing a method for producing dialkylaminosilane according to the invention, wherein 1 represents a 5-neck flask, 2 represents a reflux head, 3 represents a condenser tube, 4 represents a stirrer, 5 represents a thermometer, 6 represents a gas feed port, 7 represents a sampling tube, 8 represents a magnetic stirrer, 9 represents oil bath, and 10 represents exhaust.

EXAMPLES

Hereinafter, the invention will be described more specifically by describing Examples and Comparative Examples thereof, but the invention is not limited thereto.

Example 1

Into a 2 L 5-neck flask, 300 g of n-octane and 210 g of acetonitrile were charged. An oil bath was heated to 120° C. while stirring the resulting mixture into a reflux state, and then 64 g of acetonitrile containing a large amount of water accumulated in a reflux head was removed, and the resulting content was cooled. When an internal temperature was decreased to room temperature, 325 g of trimethylchlorosilane was charged into the 5-neck flask. Dimethylamine was fed from a gas phase part of the flask thereinto at a rate of 560 mL per minute for 4 hours at room temperature. A temperature of a reaction liquid was gradually increased up to 55° C. by an exothermic reaction. When loss of trimethylchlorosilane in a raw material was confirmed by a decrease in the temperature of the reaction liquid and gas chromatography (GC), feed of dimethylamine was stopped. A temperature of the oil bath was set to 80° C., and the resulting material was refluxed and aged for 1 hour. After cooling, 1040 g of the reaction liquid was obtained.

The reaction liquid was filtered by a pressure filter, and a residue was washed with 50 g of acetonitrile to obtain 754 g of a filtrate. The filtrate was separated into a n-octane layer and an acetonitrile layer, and therefore was separated by a separating funnel to obtain 617 g of n-octane layer containing dimethylaminotrimethylsilane. When a GC analysis was conducted, 280 g of dimethylaminotrimethylsilane was contained therein and a reaction yield was 80%. Further, when hydrolyzable chlorine was measured, a content was 4 ppm.

As a dehalogenation (chlorination) agent, 16 mg of potassium tert-butoxide, twice as many as moles of a chlorine component, was added to the n-octane layer, and a rectifying column prepared by packing HELI PACK into a column having a diameter of 2.5 cm and a length of 1 m was used at ordinary pressure to obtain 196 g of dimethylaminotrimethylsilane having a purity of 99% or more and a hydrolyzable chlorine component less than 1 ppm with a distillation yield of 70%.

Comparative Example 1

Into a 2 L 5-neck flask, 450 g of pseudocumene (1,2,4-trimethylbenzene) was charged. Dewatering treatment was not applied thereto, and while the resulting mixture was stirred, 38 g of trimethylchlorosilane was charged into the 5-neck flask at room temperature. Dimethylamine was fed from a gas phase part of the flask thereinto at a rate of 100 mL per minute for 2.5 hours at room temperature. A temperature of a reaction liquid was gradually increased up to 35° C. by an exothermic reaction. When loss of trimethylchlorosilane in a raw material was confirmed by a decrease in the temperature of the reaction liquid and a GC analysis, feed of dimethylamine was stopped. A temperature of the oil bath was set to 80° C., and the resulting material was aged for 1 hour. Then, 510 g of the reaction liquid was obtained.

The reaction liquid was filtered by a pressure filter, and a residue was washed with 50 g of pseudocumene to obtain 470 g of a filtrate. When the GC analysis was conducted, 16 g of dimethylaminotrimethylsilane was contained and a reaction yield was 40%. Further, when hydrolyzable chlorine was measured, a content was 35 ppm. As a dehalogenation (chlorination) agent, 530 mg of potassium tert-butoxide, twice as many as moles of a chlorine component, was added to the filtrate, and a rectifying column prepared by packing HELI PACK into a column having a diameter of 2.5 cm and a length of 1 m was used at ordinary pressure to obtain 8 g of dimethylaminotrimethylsilane having a purity of 95% and a hydrolyzable chlorine component less than 1 ppm with a distillation yield of 52%.

Comparative Example 2

Into a 2 L 5-neck flask, 450 g of pseudocumene was charged. Dewatering treatment was not applied thereto, and while the resulting mixture was stirred, 325 g of trimethylchlorosilane was fed into the 5-neck flask at room temperature. Dimethylamine was fed from a gas phase part of the flask thereinto at a rate of 560 mL per minute for 3 hours at room temperature. A temperature of a reaction liquid was gradually increased up to 51° C. by an exothermic reaction. Feed of dimethylamine was stopped even on the way of the reaction, when an amount of precipitation of dimethylamine hydrochloride was large and a liquid component was consumed, and stirring was unable to be made. An amount of dripping dimethylamine at the above time point was 202 g. The reaction liquid was in a state in which removal from the flask and filtration were unable to be performed, and therefore no dimethylaminotrimethylsilane was obtained.

Example 2

Into a 2 L 5-neck flask, 300 g of n-heptane and 210 g of acetonitrile were charged. An oil bath was heated to 120° C. while stirring the resulting mixture into a reflux state, and then 60 g of acetonitrile containing a large amount of water accumulated in a reflux head was removed, the resulting content was cooled. When an internal temperature was decreased to room temperature, 135 g of trimethylchlorosilane was charged into the 5-neck flask. Dimethylamine was fed from a gas phase part of the flask thereinto at a rate of 560 mL per minute for 4 hours at room temperature. A temperature of a reaction liquid was gradually increased up to 58° C. by an exothermic reaction. When loss of chlorobismethylaminosilane was confirmed by a decrease in the temperature of the reaction liquid and a GC analysis, feed of dimethylamine was stopped. A temperature of the oil bath was set to 80° C., and the resulting material was refluxed and aged for 1 hour. After cooling, 851 g of the reaction liquid was obtained.

The reaction liquid was filtered by a pressure filter, and a residue was washed with 50 g of acetonitrile to obtain 489 g of a filtrate. The filtrate was separated into an n-octane layer and an acetonitrile layer, and therefore was separated by a separating funnel to obtain 349 g of the n-octane layer containing trisdimethylaminosilane. When the GC analysis was conducted, 104 g of trisdimethylaminosilane was contained therein and a reaction yield was 65%. Further, when hydrolyzable chlorine was measured, a content was 62 ppm.

As a dehalogenation (chlorination) agent, 136 mg of potassium tert-butoxide, twice as many as moles of a chlorine component, was added to the n-octane layer, and a rectifying column prepared by packing HELI PACK into a column having a diameter of 2.5 cm and a length of 1 m was used at ordinary pressure under reduced pressure conditions from 26.6 kPa to 6.6 kPa to obtain 64 g of trisdimethylaminosilane having a purity of 99% or more and a hydrolyzable chlorine component less than 1 ppm with a distillation yield of 63%.

Example 3

Into a 2 L 5-neck flask, 400 g of n-heptane and 58 g of metal magnesium were charged. An oil bath was heated to 120° C. while stirring the resulting mixture into a reflux state for 1 hour to allow moisture in an apparatus to react with magnesium, and the resulting content was cooled. When an internal temperature was decreased to room temperature, 217 g of trimethylchlorosilane was charged into the 5-neck flask. Dimethylamine was fed from a gas phase part of the flask thereinto at a rate of 560 mL per minute for 5 hours at room temperature. A temperature of a reaction liquid was gradually increased up to 63° C. by an exothermic reaction. When flowability of a reaction mixture was deteriorated, feed of dimethylamine was once stopped, and the oil bath was adjusted to 95° C. to heat the reaction mixture. Dimethylamine hydrochloride reacted with magnesium, and hydrogen, dimethylamine and magnesium chloride were produced. When the flowability of the reaction mixture was improved, a temperature of the oil bath was decreased to 50° C., and dimethylamine was again fed at a rate of 560 mL per minute for 5 hours. Feed of dimethylamine was once again stopped, and the oil bath was heated to 95° C. to allow dimethylamine hydrochloride to react with magnesium. When loss of chlorobismethylaminosilane was confirmed by a GC analysis, the resulting content was cooled to 50° C. Here, 100 g of acetonitrile was added thereto, and the resulting material was aged for 1 hour. After cooling, 1082 g of a reaction liquid was obtained.

The reaction liquid was filtered by a pressure filter, and a residue was washed with 200 g of n-heptane to obtain 752 g of a filtrate. When the GC analysis was conducted, 195 g of trisdimethylaminosilane was contained with a reaction yield of 75%. Further, when hydrolyzable chlorine was measured, a content was 59 ppm.

As a dehalogenation (chlorination) agent, 280 mg of potassium tert-butoxide, twice as many as moles of a chlorine component, was added to the filtrate, and a rectifying column prepared by packing HELI PACK into a column having a diameter of 2.5 cm and a length of 1 m was used under reduced pressure conditions from 26.6 kPa to 6.6 kPa to obtain 146 g of dimethylaminotrimethylsilane having a purity of 99% or more and a hydrolyzable chlorine component less than 1 ppm with a distillation yield of 75%.

Comparative Example 3

Into a 2 L 5-neck flask, 450 g of pseudocumene was charged. Dewatering treatment was not applied thereto, and while the resulting mixture was stirred, 135 g of trichlorosilane was charged into the 5-neck flask at room temperature. Dimethylamine was fed from a gas phase part of the flask thereinto at a rate of 560 mL per minute for 2.5 hours at room temperature. A temperature of a reaction liquid was gradually increased up to 48° C. by an exothermic reaction. Feed of dimethylamine was stopped even on the way of the reaction, when an amount of precipitation of dimethylamine hydrochloride was large and a liquid component was consumed, and stirring was unable to be made. An amount of dripping dimethylamine at the above time point was 169 g. The reaction liquid was in a state in which removal from the flask and filtration were unable to be performed, and therefore no trisdimethylaminosilane was obtained.

TABLE 1

|  | Example 1 | Comparative Example 1 | Comparative Example 2 |
|---|---|---|---|
| Trimethylchlorosilane | 325 g | 38 g | 325 g |
| Dimethylamine | 269 g | 37 g | Stopped at 202 g |
| Solvent 1 | Octane 300 g | Pseudocumene 450 g | Pseudocumene 450 g |
| Solvent 2 | Acetonitrile 210 g | — | — |
| Yield | 80% | 40% | Stopped on the way of reaction |
| Chlorine component after reaction | 4 ppm | 35 ppm | — |

TABLE 2

|  | Example 2 | Example 3 | Comparative Example 3 |
|---|---|---|---|
| Trichlorosilane | 135 g | 217 g | 135 g |
| Dimethylamine | 271 g | 209 g | Stopped at 169 g |
| Magnesium | — | 58 g | — |
| Solvent 1 | n-heptane 300 g | n-heptane 400 g | Pseudocumene 450 g |
| Solvent 2 | Acetonitrile 210 g | Acetonitrile 100 g | — |
| Yield | 65% | 75% | Stopped on the way of reaction |
| Chlorine component after reaction | 62 ppm | 59 ppm | — |

As is obvious from Table 1 and Table 2, comparison of Examples 1, 2 and 3 with Comparative Examples 1, 2 and 3 shows that, in Comparative Examples, the reaction was unable to be continued on the way thereof, or no product was able to be obtained unless the reaction was performed by significantly reducing volumetric efficiency of the reaction. In contrast, in Examples, dimethylaminotrimethylsilane was confirmed to be able to be produced, in which a load of filtration was reduced by reduction of production of salt, or no solid-liquid separation operation such as decantation was required, and the volumetric efficiency of the reaction was high.

What is claimed is:

1. A method for producing dialkylaminosilane, by allowing dialkylamine to react with chlorosilane in a mixed solvent of an aprotic polar solvent and a solvent of straight-chain or branched hydrocarbon,
wherein the aprotic polar solvent is at least one selected from acetonitrile, dimethylformamide, acetone, dichloromethane, dimethyl sulfoxide, dimethylacetamide and hexamethylphosphoramide.

2. The method for producing dialkylaminosilane according to claim 1, wherein metal is added thereto in a reaction of dialkylamine with chlorosilane.

3. The method for producing dialkylaminosilane according to claim 1, wherein the solvent of straight-chain or branched hydrocarbon is used in an amount of 0.2 to 10 times in weight based on chlorosilane.

4. The method for producing dialkylaminosilane according to claim 1, wherein the aprotic polar solvent is used in an amount of 0.2 to 10 times in weight based on chlorosilane.

5. The method for producing dialkylaminosilane according to claim 1, wherein the dialkylamine is a compound of the following formula:

wherein, R1 and R2 are independently a straight-chain alkyl group having 1 to 6 carbons, a branched alkyl group having 3 to 6 carbons or a phenyl group.

6. The method for producing dialkylaminosilane according to claim 1, wherein the chlorosilane is a compound of the following formula:

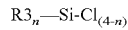

wherein, R3 is hydrogen, a straight-chain alkyl group having 1 to 6 carbons, a branched alkyl group having 3 to 6 carbons or a phenyl group, and n is an integer from 0 to 3.

7. The method for producing dialkylaminosilane according to claim 1, wherein the aprotic polar solvent is acetonitrile.

8. The method for producing dialkylaminosilane according to claim 1, wherein the solvent of straight-chain or branched hydrocarbon is straight-chain hydrocarbon having 5 to 40 carbons or branched hydrocarbon having 5 to 40 carbons.

9. The method for producing dialkylaminosilane according to claim 2, wherein the metal to be added is at least one selected from magnesium, calcium and zinc.

* * * * *